(12) United States Patent
Deane

(10) Patent No.: US 11,590,069 B1
(45) Date of Patent: *Feb. 28, 2023

(54) PET CLEANSING COMPOSITION

(71) Applicant: Jeffrey Alan Deane, Los Angeles, CA (US)

(72) Inventor: Jeffrey Alan Deane, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/070,897

(22) Filed: Nov. 4, 2013

(51) Int. Cl.
A61K 8/97 (2017.01)
A61K 8/64 (2006.01)
A61Q 5/12 (2006.01)

(52) U.S. Cl.
CPC .................. A61K 8/97 (2013.01); A61K 8/64 (2013.01); A61Q 5/12 (2013.01)

(58) Field of Classification Search
CPC ............... A61K 8/97; A61K 8/64; A61Q 5/12
See application file for complete search history.

(56) References Cited

U.S. PATENT DOCUMENTS

| | | | |
|---|---|---|---|
| 3,503,887 A | 3/1970 | Beebe | |
| 4,358,286 A | 11/1982 | Grollier et al. | |
| 4,459,285 A | 7/1984 | Grollier et al. | |
| 4,508,714 A | 4/1985 | Cecic et al. | |
| 4,847,076 A | 7/1989 | Deshpande et al. | |
| 4,855,131 A | 8/1989 | Iris | |
| 4,906,460 A | 3/1990 | Kim et al. | |
| 5,152,990 A | 10/1992 | Miyauchi | |
| 5,167,954 A | 12/1992 | Frey | |
| 5,422,100 A | 6/1995 | Eliaz et al. | |
| 5,449,517 A | 9/1995 | Fitzjarrell | |
| 5,552,135 A | 9/1996 | Cioca et al. | |
| 5,641,480 A | 6/1997 | Vermeer | |
| 5,711,942 A | 1/1998 | Eicken et al. | |
| 5,716,605 A | 2/1998 | Onitsuka et al. | |
| 5,750,107 A | 5/1998 | Nomura | |
| 5,843,421 A | 12/1998 | Tsuru et al. | |
| 5,858,342 A | 1/1999 | Giret et al. | |
| 5,916,577 A | 6/1999 | Golz et al. | |
| 5,972,343 A | 10/1999 | Therrien | |
| 5,993,792 A | 11/1999 | Rath | |
| 6,153,196 A | 11/2000 | Kripp et al. | |
| 6,190,678 B1 | 2/2001 | Hasenoehrl et al. | |
| 6,221,372 B1 | 4/2001 | Golz-Berner et al. | |
| 6,312,675 B1 | 11/2001 | Deane | |
| 6,489,286 B1 | 12/2002 | Lukenbach et al. | |
| 6,506,375 B1 | 1/2003 | Barr | |
| 6,537,564 B1 | 3/2003 | Mabratu | |
| 6,544,534 B2 | 4/2003 | Malmgren et al. | |
| 6,607,716 B1 | 8/2003 | Smith et al. | |
| 6,723,309 B1 | 4/2004 | Deane | |
| 6,844,014 B1 | 1/2005 | Rafkin | |
| 7,338,671 B2 | 3/2008 | Golz-Berner et al. | |
| 7,771,708 B2 | 8/2010 | Hoffmann et al. | |
| 7,807,190 B2 | 10/2010 | Kingsley | |
| 7,977,290 B1 | 7/2011 | Deane | |
| 8,063,005 B2 | 11/2011 | Kalidindi | |
| 8,158,567 B1 | 4/2012 | Deane | |
| 8,293,286 B2 | 10/2012 | Nouvel | |
| 8,309,143 B2 | 11/2012 | Campbell et al. | |
| 8,318,143 B2 | 11/2012 | Van Gogh et al. | |
| 8,354,099 B2 | 1/2013 | Maor | |
| 2001/0051142 A1 | 12/2001 | Duden et al. | |
| 2002/0150547 A1 | 10/2002 | Lee et al. | |
| 2002/0155086 A1 | 10/2002 | Verdun et al. | |
| 2002/0183217 A1 | 12/2002 | Perron et al. | |
| 2003/0147842 A1 | 8/2003 | Restle et al. | |
| 2003/0165582 A1 | 9/2003 | Pauly et al. | |
| 2003/0228272 A1 | 12/2003 | Amjad et al. | |
| 2004/0146481 A1 | 1/2004 | Busch et al. | |
| 2004/0052756 A1 | 3/2004 | Taguchi et al. | |
| 2004/0102354 A1 | 5/2004 | Fack et al. | |
| 2004/0105833 A1 | 6/2004 | Fack et al. | |
| 2004/0116311 A1* | 6/2004 | Luo .......................... A61K 8/86 510/119 |
| 2004/0185024 A1 | 9/2004 | Maubru | |
| 2004/0202686 A1 | 10/2004 | Welch | |
| 2005/0009716 A1 | 1/2005 | Piterski et al. | |
| 2005/0069511 A1 | 3/2005 | Magnet et al. | |
| 2005/0101499 A9 | 5/2005 | Lazzeri et al. | |
| 2005/0129743 A1 | 6/2005 | Benjamin et al. | |
| 2005/0169869 A1 | 8/2005 | Laurent et al. | |
| 2005/0170023 A1 | 8/2005 | De La Mettrie | |
| 2005/0196367 A1 | 9/2005 | Ohta et al. | |

(Continued)

FOREIGN PATENT DOCUMENTS

JP 58004710 A * 6/1981

OTHER PUBLICATIONS

Anonymous. Tri-K Industries [online]; 2010; downloaded from <URL http://www.scsformulate.co.uk/wp-content/uploads/2015/08/Rice-Proteins-Brochure.pdf> on May 20, 2016; 3 pages.*
Oshimura et al. J. Cosmet. Sci. 2007; 58: 347-357.*
Anonymous. Int J Toxicol. 2006; 25(2): abstract.*
Kasper, Robin, "The Groomer Explains What pH Balance for Dogs Really Means", Ezine articles, http://ezinearticles.com, retrieved via Internet on Jun. 14, 2013, 1 page.
"Final Safety Assessment for PCA and Sodium PCA1," International Journal of Toxicology, 18 (Suppl. 1):25-34, 1999 (10 pages).

* cited by examiner

Primary Examiner — David Browe

(74) Attorney, Agent, or Firm — Womble Bond Dickinson (US) LLP

(57) ABSTRACT

A composition and method are provided. The composition may be a cleansing and conditioning composition for an animal. The composition may include, a solvent, a thickening agent, a conditioning agent comprising a rice protein, and a botanical agent. The composition may be free of a lathering agent and suitable for use in cleansing and conditioning an animal.

1 Claim, No Drawings

(56) References Cited

U.S. PATENT DOCUMENTS

| | | |
|---|---|---|
| 2005/0249689 A1 | 11/2005 | Kuo et al. |
| 2006/0018980 A1 | 1/2006 | Lee |
| 2006/0182702 A1 | 8/2006 | Lazzeri et al. |
| 2006/0272105 A1 | 12/2006 | Molenda et al. |
| 2006/0286062 A1 | 12/2006 | Schep et al. |
| 2007/0065395 A1 | 3/2007 | Kim |
| 2007/0104672 A1 | 5/2007 | Decoster et al. |
| 2007/0110705 A1 | 5/2007 | Marinos |
| 2007/0134186 A1 | 6/2007 | Mezure et al. |
| 2007/0154441 A1 | 7/2007 | Gawtrey et al. |
| 2007/0160547 A1 | 7/2007 | Duffy et al. |
| 2007/0184123 A1 | 8/2007 | Soulimani |
| 2007/0202062 A1 | 8/2007 | Workman et al. |
| 2007/0224156 A1 | 9/2007 | de Vos |
| 2007/0275021 A1 | 11/2007 | Lee et al. |
| 2007/0286908 A1 | 12/2007 | Clampitt |
| 2008/0044370 A1 | 2/2008 | Goino et al. |
| 2008/0096783 A1 | 4/2008 | Lin |
| 2008/0152605 A1 | 6/2008 | Mahe et al. |
| 2008/0193387 A1 | 8/2008 | De Wolff |
| 2008/0260867 A1 | 10/2008 | Nam |
| 2009/0004122 A1 | 1/2009 | Modak et al. |
| 2009/0056734 A1 | 3/2009 | Bacon |
| 2009/0074696 A1 | 3/2009 | Biganska et al. |
| 2010/0215726 A1* | 8/2010 | Roth ................. A61K 8/64 |
| | | 424/450 |
| 2011/0052735 A1 | 3/2011 | Zur Wiesche et al. |
| 2011/0081392 A1 | 4/2011 | de Arruda et al. |
| 2011/0150786 A1 | 6/2011 | Desenne et al. |
| 2011/0165270 A1 | 7/2011 | Glinn-Tanner |
| 2011/0168200 A1 | 7/2011 | Bourdin et al. |
| 2011/0236324 A1 | 9/2011 | Deo |
| 2011/0256249 A1* | 10/2011 | Campbell ......... A61K 8/368 |
| | | 424/735 |
| 2011/0311655 A1 | 12/2011 | Ross |
| 2012/0065115 A1 | 3/2012 | Johnson |
| 2012/0080045 A1 | 4/2012 | Hata |
| 2012/0141404 A1 | 6/2012 | Cannell et al. |
| 2012/0195870 A1 | 8/2012 | Herrmann et al. |
| 2012/0204894 A1 | 8/2012 | Odoms |
| 2012/0214746 A1 | 8/2012 | Dal Farra et al. |
| 2012/0246851 A1 | 10/2012 | Smith, III et al. |
| 2012/0263704 A1 | 10/2012 | Sugiyama |
| 2012/0276025 A1 | 11/2012 | Florence et al. |
| 2012/0282194 A1 | 11/2012 | Florence et al. |
| 2013/0058884 A1 | 3/2013 | Yalcin |

PET CLEANSING COMPOSITION

BACKGROUND

Field

Cleansing compositions. More specifically, a cleansing and conditioning composition for pets.

Background

There are a wide variety of products on the market for cleaning and moisturizing pets, for example, dogs, cats, horses and other similar domesticated animals that serve as human companions. Pet cleansers include cleaning agents which are typically chemicals intended to remove dirt, oil, dead skin cells and other types of pollutants from the skin and/or fur coat. Such chemicals may include detergents and/or surfactants such as Sodium Lauryl Sulphate (SLS) or Sodium Laureth Sulphate (SLES). When applied to the skin and/or fur in combination with water, the cleansers provide a lathering effect. Many consumers associate lathering with cleaning therefore many cleansers include surfactants with strong lathering properties. These chemical cleaning agents, however, also strip the skin and fur of natural oils and moisture during the cleaning process. In the case of pets with sensitive skin, such chemicals can be particularly irritating to the pet and cause much discomfort.

DETAILED DESCRIPTION

In one embodiment, the cleansing composition disclosed herein is a universal cleansing conditioner designed to be gentle, while still thoroughly cleansing and moisturizing the hair and/or skin of the user, for example, a pet. In some embodiments, the composition is a non-lathering formulation which is pH balanced for pets and includes a combination of botanical agents (e.g. botanical extracts and essential oils), amino acids, peptides, vitamins, and nutrients. In addition, the composition may be free of lathering agents, harsh detergents and chemicals (e.g., SLS and SLES) which can irritate and strip the skin and fur of natural oils and moisture. Instead, the composition may include a conditioning agent such as rice protein, which alone, or in combination with other conditioning agents or emulsifiers, provides a safe and effective cleansing component for cleaning and conditioning, for example, the fur and/or skin on pets without any lathering. In some cases, the conditioning agent and/or emulsifier may form a cationic cleaning composition, which effectively cleanses pets without harsh detergents and chemicals. In some embodiments, the composition may be a cleanser and conditioner all in one.

The term "botanical agent" as used herein refers to plant derived products such as plant extracts and essential oils derived from plants.

In some embodiments, the composition is in the form of a body care product, including, without limitation, a cleansing conditioner, particularly a fur cleansing conditioner. In some embodiments, the composition is in the form of a foam, a cream, a lotion, a scrub or a gel. The composition may be in any form suitable for application to, and cleansing and/or conditioning of, a pet.

In one embodiment, the composition is a concentrated formulation which can be diluted, such as with water, prior to applying the composition to the subject. Representatively, in one embodiment, the concentrated formulation may be diluted prior to application to a pet such that the ratio of formulation to diluent is about 2:3. Representatively, where the formulation is to be used on a small pet (e.g. up to 25 pounds), approximately 2 ounces of the concentrated formulation may be diluted with 3 ounces of water. In another embodiment, where the formulation is to be used on a medium size pet (e.g. 25-50 pounds), approximately 4 ounces of the concentrated formulation may be diluted with 6 ounces of water. In still further embodiments, where the formulation is to be used on a large size pet (e.g. 50-100 pounds), approximately 6 ounces of the formulation may be diluted with 9 ounces of water.

The composition may be pH balanced for use on animals such as pets including dogs, horses and the like. In this aspect, the composition is less drying to the pet than typical pet cleansers, many of which are not pH balanced for a pet's skin and coat. Rather, the composition disclosed herein is pH balanced to the pet's skin and coat. For example, the composition may have a pH of from about 5 to about 7.5 or from about 5.5 to about 7.

In some embodiments, the composition may be applied to the fur or coat of a pet (e.g. a dog or a horse) after the coat has been soaked with water. Any amount of the composition which thoroughly saturates the coat can be applied. Additional water can be added and the water and composition are then massaged into the coat of the animal, such as with the hands of the user or a brush. In some embodiments, the composition may be left on the animal for several minutes (e.g. 3-5 minutes) in order to ensure the composition has thoroughly worked itself through the coat of the animal. The composition is then rinsed from the animal with water. The composition is gentle enough to be used to cleanse and/or condition the pet as frequently as needed, for example, as often as once a week, or once every couple weeks.

The composition may include several key ingredients in amounts, which in combination, work synergistically to remove dirt, unwanted contaminants and pests from the fur without stripping the fur of its natural oils. Some of the ingredients further add or restore moisture to the fur and/or skin. The combination of ingredients are specifically selected and combined to form a composition, for example a cleansing and conditioning composition, which is safe and effective for use on pets.

Representatively, the composition may include a combination of one or more of a solvent(s), thickening agent(s), conditioning agent(s), botanical agent(s) and amino acid(s). The composition may further include a peptide(s). Additionally, the composition may include a combination of one or more of a humectant(s), moisturizing agent(s), emulsifier(s), fragrance(s), preservative(s), acidifier(s), emollient(s), vitamin(s), nutrient(s), chelating agent(s), and antiseptic(s).

In one embodiment, the composition balances one or more solvent(s), thickening agent(s), conditioning agent(s), botanical agent(s), amino acid(s), peptide(s), humectant(s), moisturizing agent(s), emulsifier(s), fragrance(s), preservative(s), acidifier(s), emollient(s), vitamin(s), nutrient(s), chelating agent(s), and antiseptic(s) in amounts sufficient to provide a composition that effectively cleanses and conditions the fur of an animal, for example, a pet.

Representatively, a balanced composition includes from at least 30%, for example, from about 30 percent (%) to about 100% by weight solvent(s), from about 3.01% to 10.1% by weight thickening agent(s), from about 1.4% to 4.3% by weight conditioning agent(s), from about 0.15% to 1.5% by weight botanical agent(s), from about 0.11% to 1.1% by weight amino acid(s), from about 0.61% to 2.1% by weight humectant(s), from about 1% to 3% by weight moisturizing agent(s), from about 0.31% to 1.1% by weight emulsifier(s), from about 0.45% to 1.8% by weight fragrance(s), from about 0.22% to 0.8% by weight preservative(s), from about 0.1% to 0.3% by weight acidifier(s), from about 0.1% to 1% by weight emollient(s) (a portion of which may be made up of peptides), from about 0.01% to 0.1% by weight vitamin(s), from about 0.01% to 0.1% by weight nutrient(s), from about 0.01% to 0.1% by weight chelating agent(s), and from about 0.01% to 0.1% by weight antiseptic(s) in amounts sufficient to provide a composition that effectively cleanses and conditions the fur of an animal, for example, a domesticated animal such as a pet. In other embodiments, the composition can contain any one or more of the agents disclosed herein, in any amounts and any combinations.

A representative solvent(s) may include, but is not limited to, water.

A representative thickening agent(s) may include, but is not limited to, a cetearyl alcohol, which may be plant derived, and a carbomer. Fur conditioning products work best when the conditioning composition is applied evenly throughout the fur. Plant derived cetyl alcohol facilitates this process by providing a creamy texture to the composition disclosed herein. The texture and overall richness in the feeling of the composition is believed to increase the efficiency and uniformity of the application, resulting in more of the fur receiving appropriate levels of the composition. Carbomers help to stabilize the composition and give it texture.

A representative conditioning agent(s) may include, but is not limited to, Cocodimonium Hydroxypropyl Hydrolyzed Rice Protein, Behentrimonium Methosulfate and Stearmidopropyl Dimethylamine. Cocodimonium Hydroxypropyl Hydrolyzed Rice Protein is a wheat and soy free protein source with a better vitamin and mineral profile than both wheat and soy proteins. Cocodimonium Hydroxypropyl Hydrolyzed Rice Protein may be used to condition the fur and generally improve the overall fur health.

A representative botanical agent(s) may include, but is not limited to, *Urtica dioica* (Nettle) Extract, *Salvia officinalis* (Sage) Leaf Extract, *Oryza sativa* (Rice Syrup) Extract, *Eucalyptus* (*Globulus*) Oil, *Avena sativa* (Oat) Kernel Extract, *Rosmarinus officinalis* (Rosemary) Leaf Extract, *Lycium barbarum* (Goji Berry) Fruit Extract, *Symphytum officinale* (Comfrey) Leaf Extract, *Panax ginseng* Root Extract, Marsh Mallow/Althea Extract, *Camellia oleifera* Leaf (Green Tea) Extract, *Calendula Officinalis* (Marigold) Flower Extract, *Bambusa Vulgaris* (Bamboo) Extract, *Aloe barbadensis* (Organic *Aloe vera*) Leaf Juice and *Rosmarinus Officinalis* (Rosemary) Leaf Oil.

*Avena sativa* (Oat) Kernel Extract is derived from oat kernels and has antioxidant properties, as well as skin conditioning properties, that can be beneficial to pets. In addition, *Avena sativa* (Oat) Kernel Extract is rich in Vitamins B1, B2 and D, which are also beneficial to pets.

*Rosmarinus officinalis* (Rosemary) Leaf Oil has purifying, cleansing and antiseptic properties. In addition, *Rosmarinus officinalis* (Rosemary) Leaf Oil is a potent source of essential fatty acids that promote blood circulation and skin health of pets.

*Aloe barbadensis* (Organic *Aloe vera*) Leaf Juice is derived from the aloe plant and has softening and conditioning properties beneficial for the overall health of the skin and fur of pets.

*Lycium barbarum* (Goji Berry) Fruit Extract contains amounts of provitamin A (beta-carotene and cryptoxanthin) which provides antioxidant properties as well as others (e.g. immunological properties) which are beneficial for the overall health of the skin and fur of pets.

*Rosmarinus officinalis* (Rosemary) Leaf Extract may be used for its antioxidant properties, which may help to stimulate the skin and help alleviate skin problems.

Some botanical agent(s) disclosed herein may also help to reduce or alleviate pet discomfort due to pests such as mites, fleas and ticks. Representatively, *Eucalyptus* (*Globulus*) Oil, *Lavandula angustifolia* (Lavender) Oil and *Melaleuca alternifolia* (Tea Tree) Leaf Oil are believed to have properties which can repel, reduce and/or alleviate pests on pets and/or the associate discomfort.

A representative amino acid(s) may include, but is not limited to, Arginine (L-Arginine), Aspartic Acid (L-Aspartic Acid), Glycine (Naturally Derived), Alanine (L-Alanine), Serine (L-Serine), Valine (L-Valine), Proline (L-Proline), Threonine (L-Threonine), Isoleucine (L-Isoleucine), Phenylalanine (L-Phenylaline) and Histidine (L-Histidine). Fur is composed of proteins which are made up of linear amino acid chains. Amino acids help build new cells and play important roles in metabolism. It is therefore believed that amino acids may have an effect on fur growth and overall fur health.

A representative humectant(s) may include, but is not limited to, Glycerin, *Crambe abyssinica* (Abyssinian) Seed Oil and Sodium 1-pyroglutamic acid (PCA). Glycerin may be a plant derived Glycerin which has natural moisturizing factors beneficial to pets. *Crambe abyssinica* (Abyssinian) Seed Oil is a natural seed oil with an ultra-light, non-greasy feel which absorbs quickly and provides superior moisturizing benefits to pets.

A representative moisturizing agent(s) may include, but is not limited to, Panthenol, also referred to herein as Pro-Vitamin B5.

A representative emulsifier(s) may include, but is not limited to, Polysorbate-60 and Polysorbate-20. One or more emulsifiers in combination with one or more conditioning agents may provide cleansing properties to the composition. In particular, the emulsifier(s) and conditioning agent(s) may, in combination, form a cationic cleaning component within the composition which effectively cleans pets in the absence of harsh chemicals or other types of cleansing components.

A representative fragrance(s) (also referred to herein as aroma), may include, but is not limited to, a parfum, *Citrus medica* Limonum (Lemon) Peel Oil, *Ocimum basilicum* (Basil) Extract, *Vanilla planifolia* Fruit Extract, *Euterpe oleracea* (Acai) Fruit Extract, *Salvia officinalis* (Sage) Oil, *Lavandula angustifolia* (Lavender) Oil and maple. It is noted that although the above extracts and oils are categorized as fragrance or aroma due to their aromatic properties, any of those which are plant derived may also be considered botanical agents. Also, in addition to their aromatic properties, many of the above-listed fragrances also have properties which are beneficial to the health of pet fur, and pets in general.

For example, *Salvia officinalis* (Sage) Oil is believed to stimulate the lymphatic system and boost glandular function while also capable of treating dermatitis, sores, ulcers and insect bites on the pet. *Citrus medica* Limonum (Lemon) Peel Oil is a natural source of Vitamin C and antioxidant bioflavonoids which can be beneficial to pets. *Citrus medica* Limonum (Lemon) Peel Oil can be beneficial in protecting skin against damage from ozone and also has anti-inflammatory properties that can help to treat and/or sooth skin inflammation. Similarly, *Ocimum basilicum* (Basil) Extract is believed to calm inflammation and swelling of the skin.

A representative preservative(s) may include, but is not limited to, Phenethyl Alcohol, Caprylyl Glycol and Methylchloroisothiazolinone Methylisothiazolinone.

A representative acidifier(s) may include, but is not limited to, Citric Acid such as a citric acid naturally derived from fruits such as lemons, oranges, limes, or other citrus fruits.

A representative emollient(s) may include, but is not limited to, *Melaleuca alternifolia* (Tea Tree) Leaf Oil, *Avena sativa* (Oat) Kernel Flour, Borage (Organic Starflower) Seed Oil, Sodium Lactate, *Oenothera biennis* (Organic Evening Primrose) Oil, *Linum usitatissimum* (Organic Linseed) Seed Oil, Soluble Collagen, PCA, Palmitoyl Oligopeptide and Palmitoyl Tetrapeptide-7.

*Oenothera biennis* (Organic Evening Primrose) Oil is an essential fatty acid, rich in Gamma Linoleic and Gamma Linolenic acids, and also known as Vitamin F. *Oenothera biennis* (Organic Evening Primrose) Oil therefore not only hydrates the skin but helps restore moisture and lipid balance to the skin.

It is further noted that although Palmitoyl Oligopeptide and Palmitoyl Tetrapeptide-7 are listed as emollients, they may also be referred to as peptides, which in addition to their emollient properties have conditioning properties which are beneficial to pets. In particular, Palmitoyl Oligopeptide is believed to enhance the production of collagen, moisturize and soften the skin. Palmitoyl Oligopeptide further includes cleansing properties. Palmitoyl Tetrapeptide-7 is believed to increases skin elasticity, firmness and tone.

A representative vitamin(s) may include, but is not limited to, Linoleic Acid (Vitamin F).

A representative nutrient(s) may include, but is not limited to, Tocopherol (Non-GMO "TocoBiol").

A representative chelating agent(s) may include, but is not limited to, Tetrasodium Glutamate Diacetate (Natural Chelate).

A representative antiseptic(s) may include, but is not limited to, Menthol.

Other agents included in the composition that are not specifically discussed above are included and described in reference to the exemplary formulation set forth below. In addition, it should further be understood that although the agents described herein are categorized according to a single function, many have multiple functions and therefore may be understood to be included under other functional categories than those listed herein.

In one embodiment, the composition may be formed by combining or mixing two or more of the following agents: Water (Aqua), Cetearyl Alcohol (Plant Derived), Behentrimonium Methosulfate, Panthenol (Pro-Vitamin B5), *Crambe abyssinica* (Abyssinian) Seed Oil, Stearamidopropyl Dimethylamine, Glycerin (Plant Derived), Polysorbate-60, Fragrance (Parfum), Cocodimonium Hydroxypropyl Hydrolyzed Rice Protein, Phenethyl Alcohol, Citric Acid (Naturally Derived), Caprylyl Glycol, *Citrus medica Limonum* (Lemon) Peel Oil, *Urtica dioica* (Nettle) Extract, *Salvia officinalis* (Sage) Leaf Extract, *Oryza sativa* (Rice Syrup) Extract, *Melaleuca alternifolia* (Tea Tree) Leaf Oil, Linoleic Acid (Vitamin F), *Eucalyptus* (*Globulus*) Oil, *Avena sativa* (Oat) Kernel Flour, *Avena sativa* (Oat) Kernel Extract, *Rosmarinus officinalis* (Rosemary) Leaf Extract, Tocopherol (Non-GMO "TocoBiol"), *Ocimum basilicum* (Basil) Extract, Tetrasodium Glutamate Diacetate (Natural Chelate), Menthol, Borage (Organic Starflower) Seed Oil, Sodium PCA, Sodium Lactate, *Oenothera biennis* (organic Evening Primrose) Oil, *Lycium barbarum* (Goji Berry) Fruit Extract, *Linum usitatissimum* (Organic Linseed) Seed Oil, Arginine (L-Arginine), *Vanilla planifolia* Fruit Extract, Aspartic Acid (L-Aspartic Acid), *Symphytum officinale* (Comfrey) Leaf Extract, Soluble Collagen, *Panax ginseng* Root Extract, Marsh Mallow/Althea Extract, *Euterpe oleracea* (Acai) Fruit Extract, *Camellia oleifera* Leaf (Green Tea) Extract, *Calendula officinalis* (Marigold) Flower Extract, *Bambusa vulgaris* (Bamboo) Extract, PCA, Glycine (Naturally Derived), Alanine (L-Alanine), Serine (L-Serine), Valine (L-Valine), Carbomer, *Aloe barbadensis* (Organic *Aloe vera*) Leaf Juice, Proline (L-Proline), Polysorbate-20, Threonine (L-Threonine), Isoleucine (L-Isoleucine), Palmitoyl Oligopeptide, Methylchloroisothiazolinone, Palmitoyl Tetrapeptide-7, Phenylalanine (L-Phenylaline), Histidine (L-Histidine), Methylisothiazolinone, *Salvia officinalis* (Sage) Oil, *Rosmarinus officinalis* (Rosemary) Leaf Oil and *Lavandula angustifolia* (Lavender) Oil In one embodiment, the composition may be formed as a concentrated cream composition having a specific gravity (SG) of 0.97, a pH of 4.66 and a viscosity of 40,000. The composition may be formed by heating a mixture of the hydrophilic ingredients to a temperature of 70 degrees Celsius. A mixture of the hydrophobic ingredients may further be heated to a temperature of 70 degrees Celsius. Each of the ingredients used in the composition may be obtained from commercial sources. The heated hydrophilic and hydrophobic mixtures may be combined while mixing with medium sheer. The mixture may be cooled to 40 degrees Celsius and any heat sensitive ingredients added. The cooled mixture with heat sensitive ingredients added may then be mixed until homogenous at room temperature.

The following example sets forth an exemplary composition that may be topically applied to a subject (e.g. the fur of an animal). The ingredient amounts disclosed in the following example are in effective amounts suitable for cleansing, conditioning and generally improving the condition of the area to which the composition is applied. The composition may have the following exemplary formulation:

Example 1

| Ingredient (INCI Name) | Function | Percent |
| --- | --- | --- |
| Water (Aqua) | Solvent | at least 30.00 |
| Cetearyl Alcohol (Plant Derived) | Thickener | 3.00-10.00 |
| Behentrimonium Methosulfate | Conditioner | 1.00-3.00 |
| Panthenol (Pro-Vitamin B5) | Moisturizer | 1.00-3.00 |
| Crambe Abyssinica (Abyssinian) Seed Oil | Humectant | 0.30-1.00 |
| Stearamidopropyl Dimethylamine | Conditioner | 0.30-1.00 |
| Glycerin (Plant Derived) | Humectant | 0.30-1.00 |
| Polysorbate-60 | Emulsifier | 0.30-1.00 |
| Fragrance (Parfum) | Aroma | 0.30-1.00 |
| Cocodimonium Hydroxypropyl Hydrolyzed Rice Protein | Conditioner | 0.10-0.30 |
| Phenethyl Alcohol | Preservative | 0.10-0.30 |
| Citric Acid (Naturally Derived) | Acidifier | 0.10-0.30 |
| Caprylyl Glycol | Preservative | 0.10-0.30 |
| Citrus Medica Limonum (Lemon) Peel Oil | Aroma | 0.10-0.30 |
| Urtica Dioica (Nettle) Extract | Botanical | 0.01-0.10 |
| Salvia Officinalis (Sage) Leaf Extract | Botanical | 0.01-0.10 |
| Oryza Sativa (Rice Syrup) Extract | Botanical | 0.01-0.10 |
| Melaleuca Alternifolia (Tea Tree) Leaf Oil | Emollient | 0.01-0.10 |
| Linoleic Acid (Vitamin F) | Vitamin | 0.01-0.10 |
| Eucalyptus (Globulus) Oil | Botanical | 0.01-0.10 |
| Avena Sativa (Oat) Kernel Flour | Emollient | 0.01-0.10 |
| Avena Sativa (Oat) Kernel Extract | Botanical | 0.01-0.10 |

-continued

| Ingredient (INCI Name) | Function | Percent |
|---|---|---|
| Rosmarinus Officinalis (Rosemary) Leaf Extract | Botanical | 0.01-0.10 |
| Tocopherol (Non-GMO "TocoBiol") | Nutrient | 0.01-0.10 |
| Ocimum Basilicum (Basil) Extract | Aroma | 0.01-0.10 |
| Tetrasodium Glutamate Diacetate (Natural Chelate) | Chelator | 0.01-0.10 |
| Menthol | Antiseptic | 0.01-0.10 |
| Borage (Organic Starflower) Seed Oil | Emollient | 0.01-0.10 |
| Sodium PCA | Humectant | 0.01-0.10 |
| Sodium Lactate | Emollient | 0.01-0.10 |
| Oenothera Biennis (ORGANIC Evening Primrose) Oil | Emollient | 0.01-0.10 |
| Lycium Barbarum (Goji Berry) Fruit Extract | Botanical | 0.01-0.10 |
| Linum Usitatissimum (Organic Linseed) Seed Oil | Emollient | 0.01-0.10 |
| Arginine (L-Arginine) | Amino Acid | 0.01-0.10 |
| Vanilla Planifolia Fruit Extract | Aroma | 0.01-0.10 |
| Aspartic Acid (L-Aspartic Acid) | Amino Acid | 0.01-0.10 |
| Symphytum Officinale (Comfrey) Leaf Extract | Botanical | 0.01-0.10 |
| Soluble Collagen | Emollient | 0.01-0.10 |
| Panax Ginseng Root Extract | Botanical | 0.01-0.10 |
| Marsh Mallow/Althea Extract | Botanical | 0.01-0.10 |
| Euterpe Oleracea (Acai) Fruit Extract | Aroma | 0.01-0.10 |
| Camellia Oleifera Leaf (Green Tea) Extract | Botanical | 0.01-0.10 |
| Calendula Officinalis (Marigold) Flower Extract | Botanical | 0.01-0.10 |
| Bambusa Vulgaris (Bamboo) Extract | Botanical | 0.01-0.10 |
| PCA | Emollient | 0.01-0.10 |
| Glycine (Naturally Derived) | Amino Acid | 0.01-0.10 |
| Alanine (L-Alanine) | Amino Acid | 0.01-0.10 |
| Serine (L-Serine) | Amino Acid | 0.01-0.10 |
| Valine (L-Valine) | Amino Acid | 0.01-0.10 |
| Carbomer | Thickener | 0.01-0.10 |
| Aloe Barbadensis (Organic Aloe Vera) Leaf Juice | Botanical | 0.01-0.10 |
| Proline (L-Proline) | Amino Acid | 0.01-0.10 |
| Polysorbate-20 | Emulsifier | 0.01-0.10 |
| Threonine (L-Threonine) | Amino Acid | 0.01-0.10 |
| Isoleucine (L-Isoleucine) | Amino Acid | 0.01-0.10 |
| Palmitoyl Oligopeptide | Emollient | 0.01-0.10 |
| Methylchloroisothiazolinone | Preservative | 0.01-0.10 |
| Palmitoyl Tetrapeptide-7 | Emollient | 0.01-0.10 |
| Phenylalanine (L-Phenylaline) | Amino Acid | 0.01-0.10 |
| Histidine (L-Histidine) | Amino Acid | 0.01-0.10 |
| Methylisothiazolinone | Preservative | 0.01-0.10 |
| Salvia Officinalis (Sage) Oil | Aroma | 0.01-0.10 |
| Rosmarinus Officinalis (Rosemary) Leaf Oil | Botanical | 0.01-0.10 |
| Lavandula Angustifolia (Lavender) Oil | Aroma | 0.01-0.10 |

Any one or more of the ingredients listed in Example 1 may be used to form a concentrated formulation which is diluted, such as with water, prior to applying the composition to the subject as previously discussed. Representatively, in one embodiment, a concentrated formulation including any one or more of the ingredients of Example 1 may be diluted prior to application such that the ratio of formulation to diluent is about 2:3. Representatively, approximately 2 ounces of a formulation including any one or more of the ingredients may be diluted with 3 ounces of water, or approximately 4 ounces of a formulation including any one or more of the ingredients may be diluted with 6 ounces of water, still further approximately 6 ounces of a formulation including any one or more of the ingredients may be diluted with 9 ounces of water.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

In the foregoing specification, the invention has been described with reference to specific embodiments thereof. It will, however, be evident that various modifications and changes can be made thereto without departing from the broader spirit and scope of the invention as set forth in the appended claims. The specification, accordingly, is to be regarded in an illustrative rather than a restrictive sense.

What is claimed is:

1. A cleansing and conditioning composition for an animal comprising:
at least 30% by weight a solvent, wherein the solvent comprises water;
3% to 10% by weight cetearyl alcohol;
1% to 3% by weight behentrimonium methosulfate;
1% to 3% by weight panthenol;
0.3% to 1% by weight *Crambe abyssinica* seed oil;
0.3% to 1% by weight stearamidopropyl dimethylamine;
0.3% to 1% by weight glycerin;
0.3% to 1% by weight polysorbate-60;
0.3% to 1% by weight fragrance agent;
0.1% to 0.3% by weight cocodimonium hydroxypropyl hydrolyzed rice protein;
0.1% to 0.3% by weight phenethyl alcohol;
0.1% to 0.3% by weight citric acid;
0.1% to 0.3% by weight caprylyl glycol;
0.1% to 0.3% by weight *Citrus medica limonum* (lemon) peel oil;
0.01% to 0.1% by weight *Urtica dioica* (nettle) extract;
0.01% to 0.1% by weight *Salvia officinalis* (sage) leaf extract;
0.01% to 0.1% by weight *Oryza sativa* extract;
0.01% to 0.1% by weight *Melaleuca alternifolia* (tea tree) leaf oil;
0.01% to 0.1% by weight linoleic acid;
0.01% to 0.1% by weight *Eucalyptus globulus* oil;
0.01% to 0.1% by weight *Avena sativa* (oat) kernel flour;
0.01% to 0.1% by weight *Avena sativa* (oat) kernel extract;
0.01% to 0.1% by weight *Rosmarinus officinalis* (rosemary) leaf extract;
0.01% to 0.1% by weight tocopherol;
0.01% to 0.1% by weight *Ocimum basilicum* (basil) extract;
0.01% to 0.1% by weight tetrasodium glutamate diacetate;
0.01% to 0.1% by weight menthol;
0.01% to 0.1% by weight borage seed oil;
0.01% to 0.1% by weight sodium pyroglutamic acid;
0.01% to 0.1% by weight sodium lactate;
0.01% to 0.1% by weight *Oenothera biennis* oil;
0.01% to 0.1% by weight *Lycium barbarum* (goji berry) fruit extract;
0.01% to 0.1% by weight *Linum usitatissimum* seed oil;
0.01% to 0.1% by weight L-arginine;
0.01% to 0.1% by weight *Vanilla planifolia* fruit extract;
0.01% to 0.1% by weight L-aspartic acid;
0.01% to 0.1% by weight *Symphytum officinale* (comfrey) leaf extract;
0.01% to 0.1% by weight collagen;

0.01% to 0.1% by weight *Panax ginseng* root extract;
0.01% to 0.1% by weight Althaea *officinalis* extract;
0.01% to 0.1% by weight *Euterpe oleracea* (acai) fruit extract;
0.01% to 0.1% by weight *Camellia oleifera* (green tea) leaf extract;
0.01% to 0.1% by weight *Calendula officinalis* (marigold) flower extract;
0.01% to 0.1% by weight *Bambusa vulgaris* (bamboo) extract;
0.01% to 0.1% by weight l-pyroglutamic acid;
0.01% to 0.1% by weight glycine;
0.01% to 0.1% by weight L-alanine;
0.01% to 0.1% by weight L-serine;
0.01% to 0.1% by weight L-valine;
0.01% to 0.1% by weight carbomer;
0.01% to 0.1% by weight *Aloe barbadensis* leaf juice;
0.01% to 0.1% by weight L-proline;
0.01% to 0.1% by weight polysorbate-20;
0.01% to 0.1% by weight L-threonine;
0.01% to 0.1% by weight L-isoleucine;
0.01% to 0.1% by weight palmitoyl oligopeptide;
0.01% to 0.1% by weight methylchloroisothiazolinone;
0.01% to 0.1% by weight palmitoyl tetrapeptide-7;
0.01% to 0.1% by weight L-phenylalanine;
0.01% to 0.1% by weight L-histidine;
0.01% to 0.1% by weight methylisothiazolinone;
0.01% to 0.1% by weight *Salvia officinalis* (sage) oil;
0.01% to 0.1% by weight *Rosmarinus officinalis* (rosemary) leaf oil; and
0.01% to 0.1% by weight *Lavandula angustifolia* (lavender) oil;
    wherein the composition is free of a lathering agent and the composition pH is from 5.5 to 7.

* * * * *